US010915721B1

(12) United States Patent
Dreselly Thomas et al.

(10) Patent No.: US 10,915,721 B1
(45) Date of Patent: *Feb. 9, 2021

(54) GRAPHICAL USER INTERFACE FEATURES FOR A MOBILE DEVICE COUPLED TO A BARCODE SCANNER

(71) Applicant: Allscripts Software, LLC, Raleigh, NC (US)

(72) Inventors: Matthew David Dreselly Thomas, Atlanta, GA (US); Wyatt Nordstrom, Raleigh, NC (US); Ariel Noel Norton, San Diego, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,687

(22) Filed: Aug. 12, 2019

Related U.S. Application Data

(63) Continuation of application No. 16/011,590, filed on Jun. 18, 2018, now Pat. No. 10,380,393, which is a continuation of application No. 15/376,882, filed on Dec. 13, 2016, now Pat. No. 10,002,273.

(60) Provisional application No. 62/405,914, filed on Oct. 8, 2016.

(51) Int. Cl.
| | |
|---|---|
| *G06K 7/10* | (2006.01) |
| *G06K 19/06* | (2006.01) |
| *G06K 7/14* | (2006.01) |
| *G16H 10/60* | (2018.01) |

(52) U.S. Cl.
CPC ....... *G06K 7/10821* (2013.01); *G06K 7/1413* (2013.01); *G06K 19/06028* (2013.01); *G06K 19/06112* (2013.01); *G16H 10/60* (2018.01)

(58) Field of Classification Search
CPC ......... G06K 7/10821; G06K 19/06112; G06K 7/1413; G06K 19/06028; G16H 10/60
See application file for complete search history.

(56) References Cited

U.S. PATENT DOCUMENTS

| | | | |
|---|---|---|---|
| 6,732,932 B2 | 5/2004 | Schuessler et al. | |
| 8,038,538 B2 | 10/2011 | Stucke, Jr. et al. | |
| 8,292,807 B2 | 10/2012 | Perkins et al. | |
| 8,668,138 B1 | 3/2014 | Schwarz et al. | |
| 8,972,047 B2 | 3/2015 | Johnson et al. | |
| 8,972,050 B2 | 3/2015 | Johnson et al. | |
| 9,607,256 B2 | 3/2017 | Hill et al. | |
| 9,665,760 B1 | 5/2017 | Lei et al. | |
| 10,002,273 B1* | 6/2018 | Dreselly Thomas | G06K 7/1413 |
| 10,380,393 B1* | 8/2019 | Dreselly Thomas | G06K 7/10821 |

(Continued)

OTHER PUBLICATIONS

"Ex Parte Quayle Action for U.S. Appl. No. 15/376,882", dated Sep. 20, 2017, 5 pages.

(Continued)

*Primary Examiner* — Seung H Lee
(74) *Attorney, Agent, or Firm* — Medley, Behrens & Lewis, LLC

(57) ABSTRACT

Described herein are various technologies pertaining to mobile computing devices that are communicatively coupled to barcode scanners. A mobile computing device is configured to provide feedback (visual and/or audible) pertaining to a scan of a barcode performed by a barcode scanner that is communicatively coupled to the mobile computing device.

20 Claims, 6 Drawing Sheets

(56) References Cited

U.S. PATENT DOCUMENTS

| | | |
|---|---|---|
| 2008/0223941 A1 | 9/2008 | Mrowiec |
| 2013/0056535 A1 | 3/2013 | Rowlandson et al. |
| 2013/0181050 A1 | 7/2013 | McConnell |
| 2014/0316812 A1 | 10/2014 | Hathorn et al. |
| 2016/0374776 A1 | 12/2016 | Spencer et al. |

OTHER PUBLICATIONS

"Response to the Ex Parte Quayle Action for U.S. Appl. No. 15/376,882", filed Oct. 6, 2017, 7 pages.
"Non-Final Office Action for U.S. Appl. No. 15/376,882", dated Dec. 7, 2017, 8 pages.
"Response to the Non-Final Office Action for U.S. Appl. No. 15/376,882", filed Dec. 31, 2017, 8 pages.
"Notice of Allowance for U.S. Appl. No. 15/376,882", dated Feb. 16, 2018, 8 pages.
"Non-Final Office Action for U.S. Appl. No. 16/011,590", dated Nov. 1, 2018, 12 pages.
"Response to the Non-Final Office Action for U.S. Appl. No. 16/011,590", filed Feb. 1, 2019, 12 pages.
"Notice of Allowance for U.S. Appl. No. 16/011,590", dated Mar. 27, 2019, 8 pages.

\* cited by examiner

GRAPHICAL USER INTERFACE FEATURES FOR A MOBILE DEVICE COUPLED TO A BARCODE SCANNER

RELATED APPLICATIONS

This application is a continuation of U.S. patent application Ser. No. 16/011,590, filed on Jun. 18, 2018, and entitled "GRAPHICAL USER INTERFACE FEATURES FOR A MOBILE DEVICE COUPLED TO A BARCODE SCANNER", which is a continuation of U.S. Pat. No. 10,002,273, issued on Jun. 19, 2018, and entitled "GRAPHICAL USER INTERFACE FEATURES FOR A MOBILE DEVICE COUPLED TO A BARCODE SCANNER", which claims the benefit of U.S. Provisional Patent Application No. 62/405,914, filed on Oct. 8, 2016, and entitled "GRAPHICAL USER INTERFACE FEATURES FOR A MOBILE DEVICE COUPLED TO A BARCODE SCANNER". The entireties of these applications are incorporated herein by reference.

BACKGROUND

In healthcare environments, mobile computing devices are often used by healthcare workers in connection with providing care to patients. For instance, an application executing on a mobile computing device can interface with an electronic health record (EHR) application, and a healthcare worker can retrieve data from the EHR and provide data to the EHR by way of the application executing on the mobile computing device.

Further, a mobile computing device can be placed in communication with a barcode scanner, which is configured to scan barcodes associated with various items. In a specific example, a barcode scanner can be coupled to a port on a mobile telephone, such that information can be exchanged between the barcode scanner and the mobile telephone. The barcode scanner-mobile computing device arrangement is often used in healthcare environments. For instance, a barcode can encode patient information, and can be attached to a patient ID card. The barcode scanner can scan the barcode, decode the encoded patient information, and provide the decoded patient information to the mobile computing device. The application executing on the mobile computing device can, upon receipt of the patient information, transmit a query to the EHR, wherein the query is configured to cause the EHR to return information about the patient, wherein such information is maintained by the EHR. In another example, a barcode can encode information about medication, and can be attached to a container for the medication. The barcode scanner can scan the barcode, decode the encoded medication information, and provide the decoded medication information to the mobile computing device. The application executing on the mobile computing device can, upon receipt of the medication information, transmit the medication information to the EHR, such that the EHR can be updated to indicate that a patient has been provided with the medication.

A healthcare enterprise may use several different types of barcode scanners, possibly manufactured by different manufacturers, where different types of barcode scanners may be used to scan barcodes of different formats. Some of these barcode scanners may have status lights, while others may not. Likewise, some of these barcode scanners may have speakers, while others may not. This results in feedback provided to healthcare workers that use barcode scanners to be inconsistent. For instance, the healthcare worker can use a first barcode scanner to scan a barcode on a patient badge, wherein the first barcode scanner includes feedback lights that inform the healthcare worker as to whether the scan was completed successfully. The healthcare worker can then use a second barcode scanner that includes no feedback lights, but instead includes speakers that output audible indicia as to whether the scan was completed successfully. This inconsistent feedback may result in items being scanned improperly without knowledge of the healthcare worker.

SUMMARY

The following is a brief summary of subject matter that is described in greater detail herein. This summary is not intended to be limiting as to the scope of the claims.

Described herein are various technologies related to providing consistent feedback to healthcare workers that utilize barcode scanners, regardless of the type of barcode scanner used. A barcode scanner is communicatively coupled to a mobile computing device, wherein the mobile computing device has an application installed thereon that interfaces with an electronic health record (EHR) application that executes on a server computing device that is in network communication with the mobile computing device. When the barcode scanner is communicatively coupled with the mobile computing device, a barcode scanner module executing on the mobile computing device ascertains the configuration of the barcode scanner. More particularly, the barcode scanner module determines whether the barcode scanner has status lights thereon, whether the barcode scanner has speakers thereon, whether the barcode scanner provides haptic feedback, etc.

When the barcode scanner scans a barcode assigned to an item in a healthcare environment, the mobile computing device is configured to generate output based upon the ascertained configuration of the barcode scanner. For instance, when the barcode scanner has status lights thereon, the barcode scanner module can cause the mobile computing device to transmit commands to the barcode scanner, where the commands cause the lights to operate based upon the scan performed by the barcode scanner. When there is a scan error, for example, the barcode scanner module can generate commands that are transmitted to the barcode scanner that cause the status lights to flash red, thereby informing the healthcare worker that there was an error in the scan. In another example, when the barcode scanner does not have status lights thereon, the barcode scanner module can cause a display of the mobile computing device to depict graphical features thereon, wherein the graphical features can provide feedback to the healthcare worker as to the status of the scan. The graphical features can emulate lights on a barcode scanner, such that, for example, a border of a certain color can be created and flashed. Hence, for instance, the barcode scanner module can cause the mobile computing device to present a red border on the display, and can further cause the red border to flash to indicate to the healthcare worker that there was a problem with the scan. Similarly, the barcode scanner module can generate signals that are configured to cause the mobile computing device to control speakers and/or haptic actuators of the mobile computing device, thereby informing a healthcare worker as to the status of a scan.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
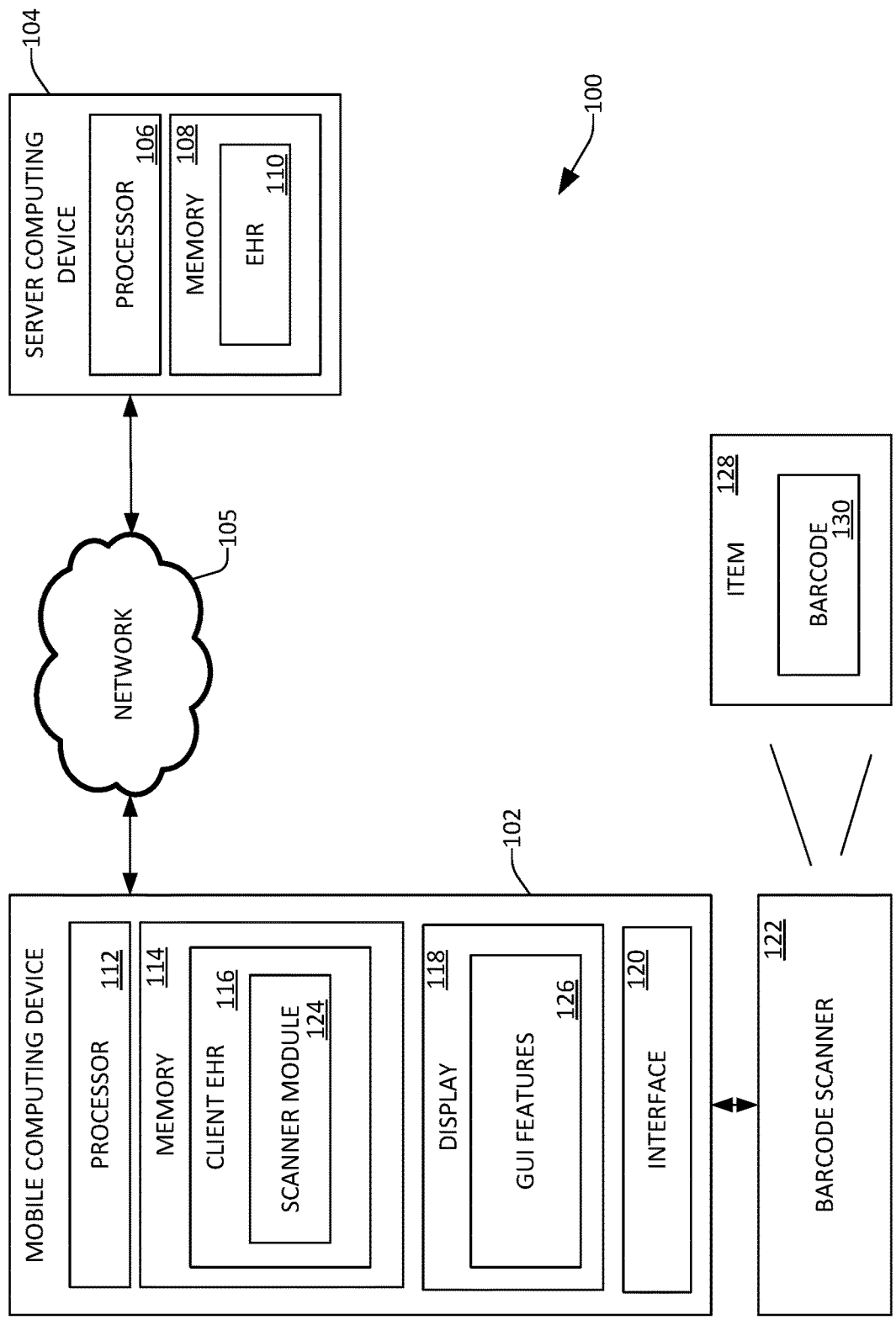
FIG. 1 is a functional block diagram of an exemplary system that facilitates providing feedback with respect to a barcode scan.

Various technologies pertaining to mobile computing devices in communication with barcode scanners are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "module," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary system 100 that facilitates providing feedback with respect to a barcode scan is illustrated. The system 100 includes a mobile computing device 102 that is in communication with a server computing device 104 by way of a network 105 (e.g., the Internet, an intranet, etc.). The mobile computing device 102 can be a mobile telephone, a tablet (slate) computing device, a media player, a wearable computing device, or the like. The server computing device includes a processor 106 and memory 108, wherein the memory 108 has an electronic health record application (EHR) 110 loaded therein, and further wherein the processor 106 executes the EHR 110. The EHR 110 can be configured to perform various tasks in a healthcare enterprise, including patient intake tasks, appointment scheduling, billing, prescription generation, patient attribute monitoring, etc.

The mobile computing device 102 includes a processor 112 and memory 114, wherein the memory 114 has a client EHR 116 loaded therein, and further wherein the processor 112 executes the client EHR 116. The client EHR 116 is generally configured to interface with the EHR 110 executing on the server computing device 104, wherein the client EHR 116 can provide data to the EHR 110 and retrieve data from the EHR 110. The mobile computing device 102 is operated by a healthcare worker (now shown), and the healthcare worker can utilize the client EHR 116 in connection with providing care to a patient or patients. For example, the mobile computing device 102 includes a display 118, and the healthcare worker can operate the mobile computing device 102 such that the client EHR 116 retrieves a portion of a patient record from the EHR 110 and causes the display 118 to display the portion of the patient record to the healthcare worker. Likewise, the healthcare worker can interact with the client EHR 116 to set forth input about the patient, and the client EHR 116 can transmit such information to the EHR 110 for storage and indexing.

The mobile computing device 102 further includes an interface 120 that is configured to interface the mobile computing device 102 with another device. The interface 120 can be a physical port, such as a universal serial bus (USB) port, a USB-C port, or other suitable port. In another example, the interface 120 can be a wireless chip, such that another device can be in communication with the mobile computing device 102 by way of a wireless connection. For instance, the interface 120 can be a Bluetooth interface, a Wi-Fi direct interface, or the like.

The system 100 further includes a barcode scanner 122 that is communicatively coupled to the mobile computing device 102 by way of the interface 120. In a non-limiting example, the barcode scanner 122 can include a sleeve (e.g., a protective sleeve) that is removably attachable to the mobile computing device 102, such that when the sleeve is attached to the mobile computing device 102, the sleeve wraps around a housing of the mobile computing device 102. Further, when the sleeve is attached the mobile computing device 102, the barcode scanner 122 is physically and electrically mated to the mobile computing device 102 by way of the interface 120. The barcode scanner 122 is configured to scan barcodes assigned to items in the healthcare environment. For instance, barcodes can be applied to patient identity cards, medicinal items, patient beds, clinician identity cards, and so forth. The barcode scanner 122 can be of an arbitrary type (e.g., an arbitrary make and model), and can be a 1-D barcode scanner or a multi-dimensional barcode scanner.

The client EHR 116 executing on the mobile computing device 102 includes a barcode scanner module 124 (referred to hereinafter as the scanner module 124). While illustrated as being a portion of the client EHR 116, it is to be understood that the scanner module 124 can be a portion of an operating system (not shown) of the mobile computing device 102, or can be an application that is separate from the client EHR 116 but is in communication with the client EHR 116. Briefly, the scanner module 124 is configured to control output interfaces (lights, speakers, etc.) of the barcode scanner 122 and/or control output interfaces of the mobile computing device 102. The scanner module 124 controls these output interfaces based upon: 1) a configuration of the barcode scanner 122; and 2) a status of a scan performed by the barcode scanner 122. For instance, the barcode scanner 122 may fail to have native lights. In such a situation, when the barcode scanner 122 is operated to scan a barcode in the healthcare environment, the scanner module 124 can cause the display 118 of the mobile computing device 102 to present graphical user interface (GUI) features 126 thereon, where the GUI features 126 indicate the status of the scan (success, fail, warning, etc.) to the healthcare worker operating the mobile computing device 102. For instance, the GUI features 126 may mimic flashing light emitting diodes (LEDs), such that the GUI features 126 act as virtual LEDs. The scanner module 124 can cause the color of the GUI features 126 to depict status of a barcode scan (red=failure, green=success, yellow=warning, blue=additional data requested, etc.). Likewise, the scanner module 124 can control a speaker of the mobile computing device 102, such that audio feedback as to the status of a scan can be presented to the healthcare worker. Similarly, the scanner module 124 can control haptic features of the mobile computing device 102, such that haptic feedback as to the status of a scan can be presented to the healthcare worker.

In another example, the barcode scanner 122 may include native output interfaces (lights, speakers, haptics etc.) integrated therein. In such a situation, the scanner module 124 can cause the mobile computing device 102 to transmit commands to be the barcode scanner 122, wherein the commands cause the barcode scanner 122 to generate outputs that are indicative of the status of a scan. These outputs are similar to those described above with respect to the mobile computing device 102. For example, the barcode scanner 122 can include LEDs (e.g., arrays of red, green, blue LEDs) that are configured to present feedback to the healthcare worker based upon a status of the scan. The scanner module 124 can receive an indication from the barcode scanner 122 as to whether a scan has been completed successfully, and the scanner module 124 (responsive to receiving this indication) can cause the mobile computing device 102 to transmit commands back to the barcode scanner 122, wherein the scans control operation of the LEDs (e.g., to provide feedback to the healthcare worker as to whether the scan completed successfully, as to whether additional data is needed, etc.).

Exemplary operation of the system 100 is now set forth. A healthcare worker operates the mobile computing device 102 such that the client EHR 116 is executed at the mobile computing device 102. In an example, the client EHR 116 is caused to present information about a patient or set of patients on the display 118. An item 128 in the healthcare environment has a barcode 130 applied thereto. The item 128, for instance, may be a medicine container, and the barcode 130 can be applied to the medicine container. In another example, the item 128 can be a patient identifier badge worn by a patient, and the barcode 130 can be on the patient identifier badge.

The barcode scanner 122 is communicatively coupled to the mobile computing device 102. Optionally, when the barcode scanner 122 is communicatively coupled to the mobile computing device 102, the scanner module 124 can determine an identity of the barcode scanner 122 (e.g., make and model), and can ascertain a configuration of the barcode scanner 122 based upon the identity of the barcode scanner 122. The configuration of the barcode scanner 122 includes indications as to: 1) whether the barcode scanner 122 has any native visual feedback lights; 2) color of any of the feedback lights of the barcode scanner; 3) whether the barcode scanner 122 has a speaker; and/or 4) whether the barcode scanner 122 is associated with haptic elements, etc.

The barcode scanner 122 is operated by the healthcare worker to scan the barcode 130, wherein information encoded in the barcode 130 is to be provided to the client EHR 116, which in turn can transmit the information (or data based upon the information) to the EHR 110 executing on the server computing device 104. The barcode scanner 122, when a scan is successful, decodes the information encoded in the barcode 130. When the barcode scanner 122 is unsuccessful when performing the scan, and is therefore unable to decode the information in the barcode 130 (e.g., due to misalignment of the barcode scanner 122 relative to the barcode 130, due to the barcode generally being unreadable, etc.), the barcode scanner 122 can transmit an error message to the mobile computing device 102. Additionally, in an exemplary embodiment, when the barcode scanner 122 has native feedback lights which are controllable only by the barcode scanner 122, the barcode scanner 122 controls the feedback lights to visually indicate whether the scan of the barcode 130 is successful or has failed.

Returning to the example where the barcode scanner 122 is unsuccessful when performing the scan and further where the barcode scanner 122 lacks feedback lights, the scanner module 124 can receive the error message from the barcode scanner 122. Responsive to receiving the error message, the scanner module 124 can cause the display 118 to present the GUI features 126 thereon. The GUI features 126 can be a flashing red border, thereby visually indicating to the healthcare worker that the scan has failed. In another exemplary embodiment, the scanner module 124 can cause the display 118 to present the GUI features 126 thereon regardless of whether the barcode scanner 122 has native feedback lights integrated therein. The scanner module 124 can perform similar acts with respect to any speakers on the mobile computing device 102 and/or the barcode scanner 122, as well as any haptic elements on the mobile computing device 102 and/or the barcode scanner 122.

In still yet another example, rather than the barcode scanner 122 controlling its own lights, the scanner module 124 can cause the mobile computing device 102 to transmit signals to the barcode scanner 122, wherein such signals control the feedback lights of the barcode scanner 122 (as well as speakers and/or haptic elements of the barcode scanner 122). Thus, when the barcode scanner 122 transmits decoded information to the mobile computing device 102, the scanner module 124 can ascertain that the barcode scanner 122 successfully completed the scan. The scanner module 124 can then cause the mobile computing device 102 to transmit control signals to the barcode scanner 122, where the control signals are configured to cause the feedback lights on the barcode scanner 122 to flash green, for example (thereby indicating to the healthcare worker operating the barcode scanner 122 that the scan was completed successfully). Alternatively, when the barcode scanner 122 transmits an error message to the mobile computing device 102 (indicating that the scan was unsuccessful), the scanner module 124 can cause the mobile computing device 102 to transmit control signals to the barcode scanner 122, wherein the control signals are configured to cause the feedback lights on the barcode scanner 122 to flash red.

In another example, the barcode scanner 122 can successfully decode the information encoded in the barcode 130, and can transmit the information to the mobile computing device 102. The mobile computing device 102 receives the decoded information, and the client EHR 116 is provided with the decoded information. The scanner module 124 receives current context of the client EHR 116 (e.g., a type of page being presented to the healthcare worker on the display 118, an identity of a patient shown on the display 118, etc.), and the scanner module 124 can ascertain whether the decoded information is consistent with the current context of the client EHR 116. For instance, when the client EHR 116 is displaying a record about a certain patient on the display 118, and the decoded information identifies a medication to which the patient is allergic, the scanner module 124 can cause the GUI features 126 to be the flashing red border, thereby indicating to the healthcare worker that there is a problem with the scan. Additionally or alternatively, the scanner module 124 can cause the mobile computing device 102 to transmit control signals to the barcode scanner 122, which control output interfaces (e.g., feedback lights) to indicate a problem with the scan. Alternatively, the scanner module 124 can cause the GUI features 126 to be a flashing yellow border, thereby indicating to the healthcare worker that the barcode scanner 122 successfully decoded the information from the barcode 130, but that some other problem exists.

In still yet another example, the barcode scanner 122 may successfully scan the barcode 130 attached to the item 128, and transmit decoded information to the mobile computing device 102. The client EHR 116 receives the decoded information, and ascertains that there is another step in a workflow to be completed, where the next step optionally includes use of the barcode scanner 122. For instance, the item 128 can be a patient identifier badge, and the barcode 130 can encode a patient identifier. The barcode scanner 122 scans the barcode 130, and transmits the decoded patient identifier to the mobile computing device 102. The client EHR 116 receives the decoded patient identifier, and transmits a query to the server computing device 104 (where the query includes or is based upon the patient identifier). The EHR 110 executes the query over a database (not shown) to generate search results, and causes the server computing device 104 to transmit the search results to the mobile computing device 102. The search results may indicate that it is time for the patient to consume a certain medication. The client EHR 116 receives such search results, and the scanner module 124 can be provided with an indication that there is another workflow step to be taken by the healthcare worker (e.g., medication is to be scanned and given to the patient). The scanner module 124, in such an example, can cause the display 118 to present the GUI features 126 thereon, wherein the GUI features 126 can include a blue flashing border, which indicates to the healthcare worker that one step in a workflow has been successfully completed, but at least one other step of the workflow remains. Again, the scanner module 124 can also construct control commands for provision to the barcode scanner 122 to control output interfaces of the barcode scanner 122.

Figure 2:
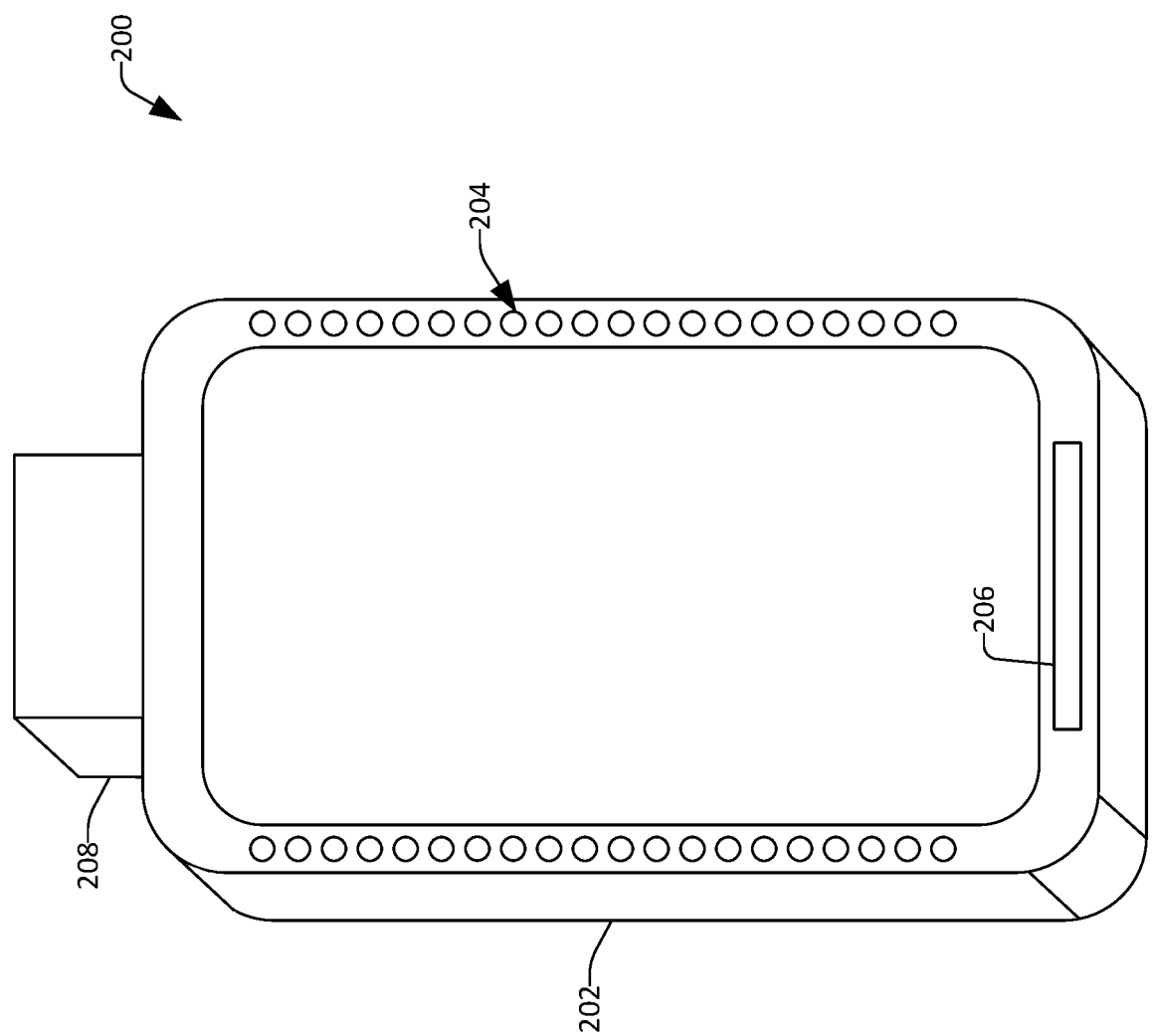
FIG. 2 is a schematic of an exemplary barcode scanner.

With reference now to FIG. 2, an exemplary barcode scanner 200 is depicted. The barcode scanner 200 includes a sleeve 202, which is configured to wrap around the housing of a mobile telephone. The sleeve 202 can be formed of a rubber, plastic, or other suitable material, and in this example form-fits around the housing of a mobile telephone. The sleeve 202 can have a plurality of LEDs (collectively depicted by reference numeral 204) incorporated into a front face of the sleeve 202. The LEDs 204 can be of different color, and can be individually controllable. For instance, the LEDs 204 can include arrays of RGB LEDs, such that the LEDs 204 can be controlled to emit light of varying colors. The sleeve 202 also includes a speaker 206 integrated therein. Further, the barcode scanner 200 comprises a scanning head 208, wherein the scanning head 208 includes a laser and at least one photoelectric cell. The scanning head 208 further comprises a circuit that is configured to convert information from the at least one photoelectric cell into computer-readable data (decoded information), and transmit such computer-readable data to a mobile computing device that is coupled to the sleeve 202.

It can be ascertained that the exemplary barcode scanner 200 includes output interfaces (the LEDs 204 and the speaker 206). When the barcode scanner 200 is coupled to the mobile computing device 102, the mobile computing device 102 can control the output interfaces as a function of a status of a scan performed by the barcode scanner 200. Additionally, to supplement such output interfaces, the scanner module 124 can cause the display 118 to present the graphical features 126 thereon as a function of the scan. In yet another example, the scanner module 124 can be configured to disable operation of the output interface of the barcode scanner 200, and instead cause the display 118 to present the graphical features 126 thereon (and optionally output audible information that is indicative of the status of the scan). An advantage of such approach is that healthcare workers are provided with consistent feedback as to barcode scans, regardless of the type of barcode scanner used. This is particularly advantageous in healthcare settings, where a healthcare worker may use several different types of barcode scanners in the scope of his or her duties.

Figure 3:
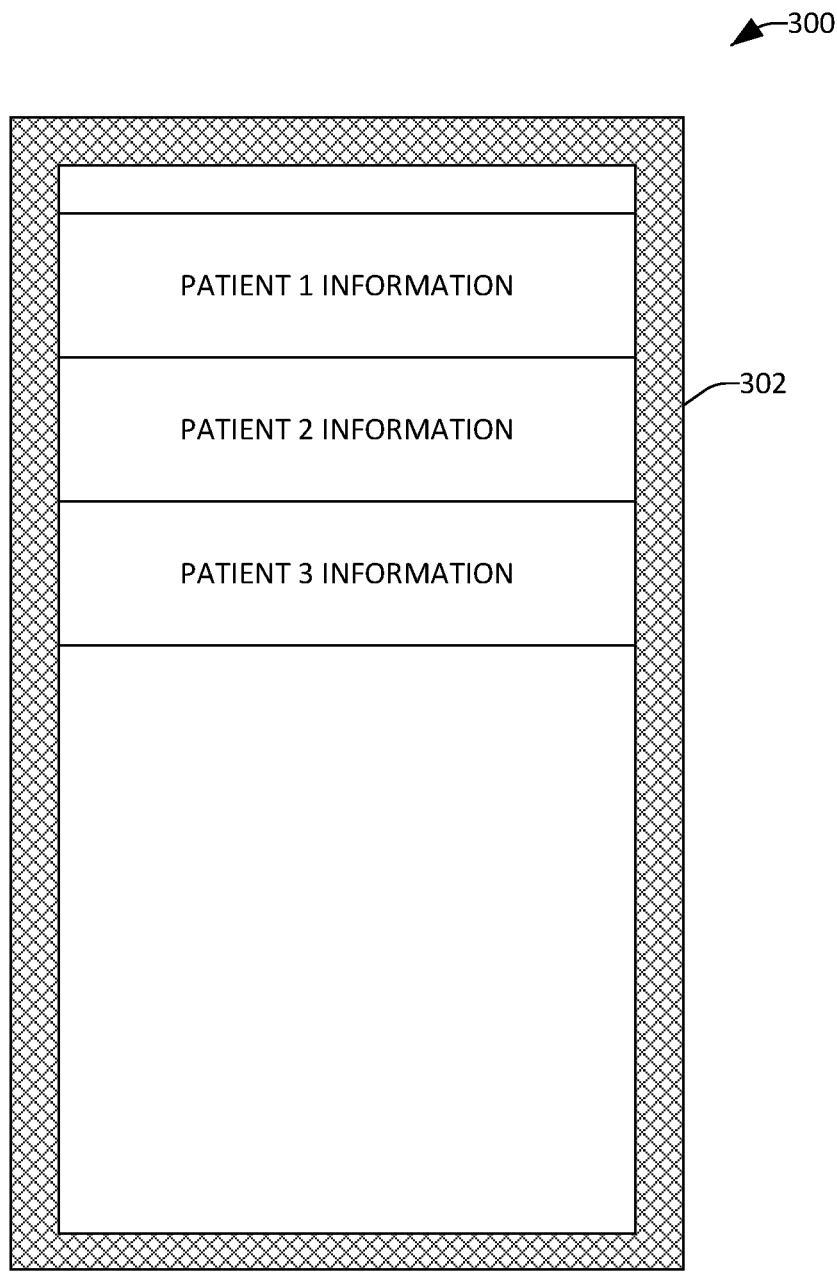
FIG. 3 illustrates an exemplary graphical user interface.

Referring now to FIG. 3, an exemplary GUI 300 that can be presented on the display 118 of the mobile computing device 102 is illustrated, where the GUI 300 includes the graphical features 126. The GUI 300 can be a GUI for the client EHR 116, and can include several bars, with each bar depicting information about a patient. The bars can include patient demographic information, an identity of a primary care physician for the patient, etc. Additionally, the GUI 300 can include a flashing border 302, which indicates the status of a scan of a barcode by the barcode scanner 122. For instance, the flashing border 302 can be red in color when there is some failure in the scan, can be green in color when the scan is successful, can be yellow in color when there is a warning pertaining to the scan, can be blue in color when additional information is needed from the healthcare worker operating the mobile computing device 102 or when there is another step to be taken in a workflow, etc. While shown as a flashing border, other implementations are contemplated. For instance, a flashing dot is contemplated, a partially transparent overlay is contemplated, etc. It is also to be understood, however, and as noted above, that the graphical features 126 are consistent, regardless of the type and/or manufacturer of the barcode scanner 122. Therefore, the healthcare worker is provided with consistent feedback regardless of the type of barcode scanner employed to scan barcodes.

Figure 4:
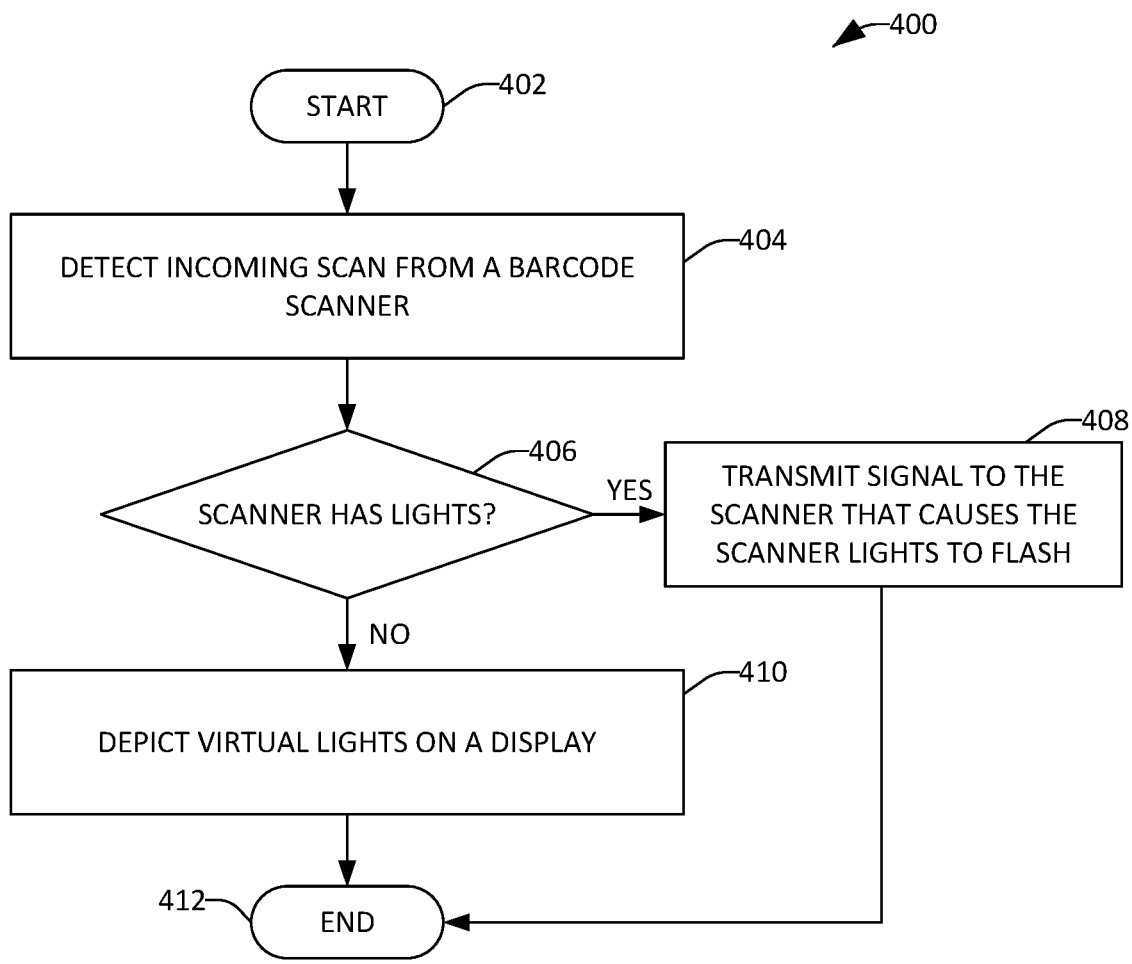
FIG. 4 is a flow diagram illustrating an exemplary methodology for providing feedback as to a barcode scan.
Figure 5:
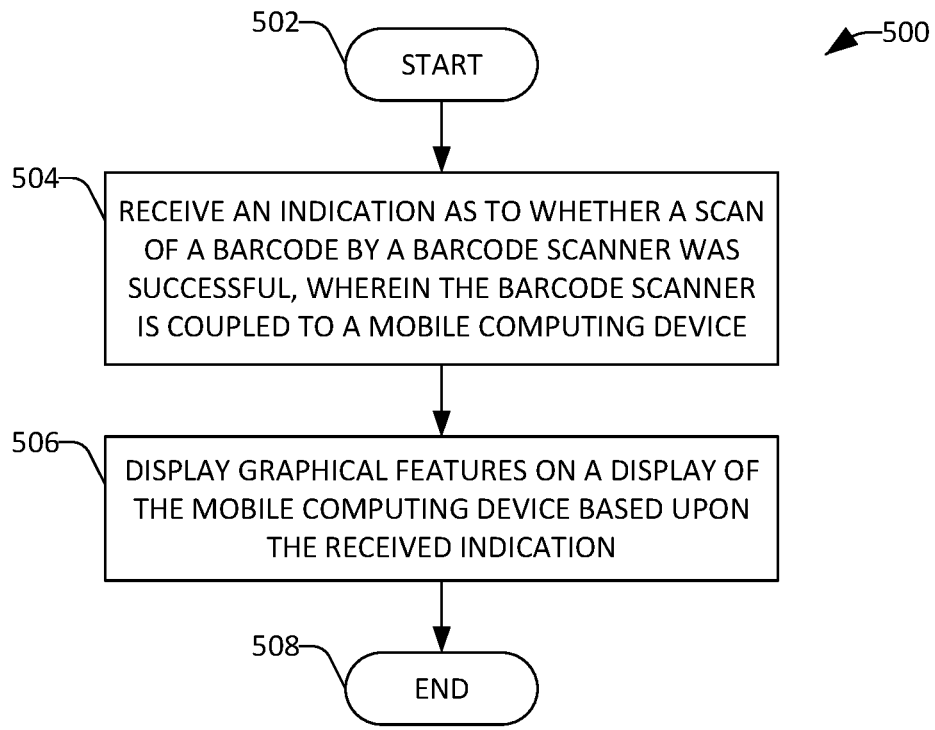
FIG. 5 is a flow diagram illustrating an exemplary methodology for rendering graphical features on a display of a mobile computing device based upon data received from a barcode scanner.

FIGS. 4-5 illustrate exemplary methodologies relating to providing feedback as to a status of a barcode scan in a healthcare environment. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Turning solely to FIG. 4, an exemplary methodology 400 that is executed at the mobile computing device 102 is depicted. The methodology 400 starts at 402, and at 404, an incoming scan is detected from a barcode scanner. The incoming scan can be detected based upon decoded information being received from the barcode scanner or an error message being received from the barcode scanner.

At 406, a determination is made as to whether the barcode scanner has feedback lights integrated therein. While the act 406 is shown as occurring subsequent to the incoming scan being detected, it is to be understood that this determination can be made prior to the incoming scan being detected (e.g., when the barcode scanner is initially communicatively coupled to the mobile computing device 102). When it is determined that the scanner has lights, at 408, the mobile computing device 102 can transmit a signal to the barcode scanner that causes the barcode scanner lights to flash. As indicated previously, the color of the lights, the duration of the flash, etc. can be dependent upon whether the scan has any errors or warnings associated therewith. Alternatively, the barcode scanner may control its own lights.

When it is determined that the scanner does not have lights, at 410, virtual lights are presented on a display of the mobile computing device 102, wherein examples of such virtual lights have been set forth above. Moreover, when the scanner does have integrated lights, the virtual lights can optionally also be presented on the display of the mobile computing device. Similar acts can be undertaken with speakers of the scanner and/or the mobile computing device, as well as haptic elements of the scanner and/or the mobile computing device. The methodology 400 completes at 412.

With regard now to FIG. 5, an exemplary methodology 500 for rendering graphical features on a display of a mobile computing device is illustrated, wherein the graphical features are indicative of a status of a scan of a barcode performed by a barcode scanner that is coupled to the mobile computing device. As described above, the mobile computing device can execute an application that receives, as input, data encoded in a barcode that has been decoded by the barcode scanner. The methodology 500 is performed by the mobile computing device, and starts at 502. At 504, an indication is received as to whether a scan of a barcode by the barcode scanner was successful. As noted above, the barcode scanner is coupled to the mobile computing device, and transmits data that indicates whether the scan was successful. This data, when the scan was successful, can include data encoded in the barcode that was decoded by the barcode scanner. In another example, this data, when the scan was unsuccessful, can include an error message, null values, or the like.

At 506, responsive to receiving the indication received at 504, and based upon such indication, graphical features are displayed on the display of the mobile computing device. The graphical features can inform an operator of the mobile computing device as to whether the scan was successful. For instance, the graphical features can be overlaid upon a GUI of the application that receives the data encoded in the barcode as input. In a more detailed example, the application can be the client EHR 116, and the graphical features can be a flashing border, such that data in the GUI of the client EHR 116 remains visible to the healthcare worker, yet the graphical features inform the healthcare worker of the status of the scan. The border can be flashed green (for some predefined period of time) when the scan was successful (and the data is consistent with the context of the application), can be flashed red (for some predefined period of time) when the scan was unsuccessful (or when the data is inconsistent with the context of the application), etc. In yet another example, the application can generate a message when another step in a workflow is to be immediately performed after provision of the data encoded in the barcode to the application. In such a case, the border can be flashed blue, to indicate to the healthcare worker that another step in the workflow is to be performed by the healthcare worker. The methodology 500 completes at 508.

Figure 6:
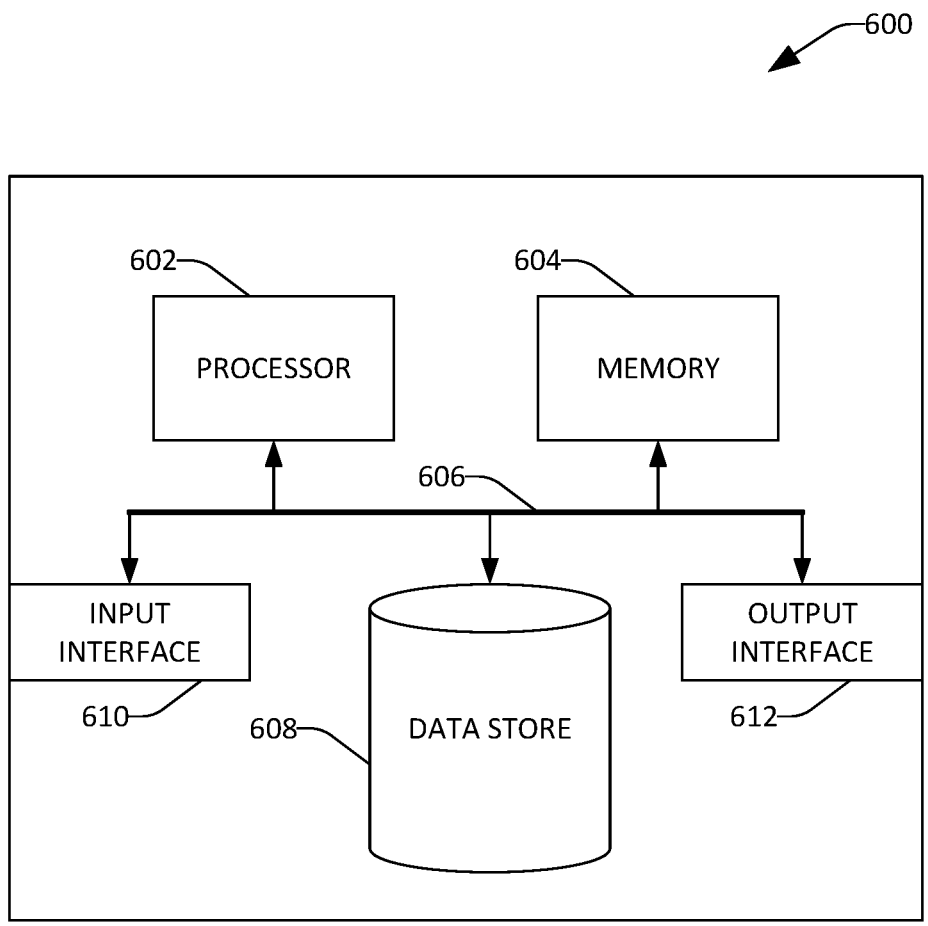
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that is configured to provide feedback as to the status of a barcode scan in a healthcare environment. By way of another example, the computing device 600 can be used in a system that executes an EHR. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store decoded information, barcode scanner identities, configurations, etc.

The computing device 600 additionally includes a data store 608 that is accessible by the processor 602 by way of the system bus 606. The data store 608 may include executable instructions, decoded information from barcodes, patient information, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A mobile computing device comprising:
a display;
a processor; and
memory storing instructions that, when executed by the processor, cause the processor to perform acts comprising:
receiving, from a barcode scanner that is external to the mobile computing device and communicatively coupled to the mobile computing device, an indication as to whether the barcode scanner successfully scanned a barcode, wherein an application executing on the mobile computing device is configured to receive data encoded in the barcode as input; and
responsive to receiving the indication and based upon the indication, causing the display to present graphical features thereon, wherein the graphical features are indicative of whether the barcode scanner successfully scanned the barcode, and further wherein the graphical features are distinct from a graphical user interface (GUI) of the application.

2. The mobile computing device of claim 1, wherein the application is a client-side electronic health record (EHR) application.

3. The mobile computing device of claim 2, wherein the indication as to the status comprises data encoded in the barcode that has been decoded by the barcode scanner, and further wherein the graphical features comprise a green graphical element to indicate to an operator of the mobile computing device that the barcode scanner has successfully scanned the barcode.

4. The mobile computing device of claim 3, wherein the green graphical element is a green border, and further wherein the green border flashes for a predefined period of time.

5. The mobile computing device of claim 2, wherein the indication as to the status comprises an error message output by the barcode scanner, and further wherein the graphical features comprise a red graphical element to indicate to an operator of the mobile computing device that the barcode scanner has failed to successfully scan the barcode.

6. The mobile computing device of claim 5, wherein the red graphical element is a red border, and further wherein the red border flashes for a predefined period of time.

7. The mobile computing device of claim 2, wherein the barcode scanner has successfully scanned the barcode, and wherein the indication as to the status comprises data encoded in the barcode that has been decoded by the barcode scanner, and further wherein the client EHR has received the data, the acts further comprising:
receiving, from the application, a message that indicates that the data is inconsistent with the context of the application, wherein the graphical features are further based upon the message.

8. The mobile computing device of claim 2, wherein the barcode scanner has successfully scanned the barcode, and wherein the indication as to the status comprises data encoded in the barcode that has been decoded by the barcode scanner, and further wherein the client EHR has received the data, the acts further comprising:
receiving, from the application, a message that indicates that an operator of the mobile computing device is to perform another step in a workflow subsequent to the barcode scanner scanning the barcode, wherein the graphical features are further based upon the message.

9. The mobile computing device of claim 1 being a mobile telephone.

10. The mobile computing device of claim 1, wherein the barcode scanner is of a first make and model, the status of the scan is that the scan was successful, and the acts further comprising:
  subsequent to the barcode scanner being decoupled from the mobile computing device, and subsequent to a second barcode scanner being coupled to the mobile computing device:
    receiving, from the second barcode scanner, a second indication as to a status of a second scan of a second barcode performed by the second barcode scanner while the second barcode scanner is coupled to the mobile computing device, wherein the second barcode scanner is of a different make and model when compared to the first barcode scanner, and further wherein the status of the second scan is that the scan was successful; and
    responsive to receiving the indication and based upon the indication, causing the display to present the graphical features thereon.

11. A method executed at a mobile computing device, the method comprising:
  receiving, from a barcode scanner that is external to the mobile computing device and in communication with the computing device, an indication as to whether a scan of a barcode by the barcode scanner was successful, wherein the mobile computing device executes an application that receives data encoded in barcodes as input; and
  responsive to receiving the indication, and based upon the indication, displaying graphical features on a display of the mobile computing device, the graphical features are configured to inform an operator of the mobile computing device as to whether the scan was successful, and further wherein the graphical features are distinct from a graphical user interface (GUI) of the application.

12. The method of claim 11, wherein the application is a client electronic health record application (EHR).

13. The method of claim 12, wherein the scan was successful, and further wherein the graphical features comprise a green graphical element.

14. The method of claim 13, wherein the graphical element is a green flashing border.

15. The method of claim 12, wherein the scan was unsuccessful, and further wherein the graphical features comprise a red graphical element.

16. The method of claim 15, wherein the graphical element is a red flashing border.

17. The method of claim 11, wherein the graphical features are consistent regardless of a make and model of the barcode scanner.

18. The method of claim 11, wherein the mobile computing device is a mobile telephone.

19. The method of claim 11, further comprising:
  prior to displaying the graphical features on the display of the mobile computing device, determining that the barcode scanner fails to include feedback lights thereon; and
  displaying the graphical features on the display only after determining that the barcode scanner fails to include the feedback lights thereon.

20. A mobile computing device comprising a computer-readable storage medium, the computer-readable storage medium comprising instructions that, when executed by a processor of the mobile computing device, cause the processor to perform acts comprising:
  receiving, from a barcode scanner that is external to the mobile computing device and in communication with the mobile computing device, an indication as to whether a scan of a barcode by the barcode scanner was successful, wherein the mobile computing device executes an application that receives data encoded in barcodes as input; and
  responsive to receiving the indication and based upon the indication, displaying graphical features on a display of the mobile telephone, the graphical features indicative of whether the scan was successful, wherein the graphical features are displayed on the display concurrently with a portion of a graphical user interface (GUI) of the application.

* * * * *